United States Patent
Bigliani et al.

[19]

[11] Patent Number: 5,876,333
[45] Date of Patent: Mar. 2, 1999

[54] ORTHOPAEDIC RETRACTOR FRAME ASSEMBLY

[75] Inventors: Louis U. Bigliani, Englewood, N.J.;
Evan L. Flatow, New York, N.Y.;
Delfreda L. Norman, Fort Wayne, Ind.;
Jeffery A. VanDiepenbos, Syracuse, Ind.; Michael Yargosz, Warsaw, Ind.

[73] Assignee: Bristol-Myers Squibb Company, New York, N.Y.; by said Delfreda L. Norman, Jeffery A. Vandiepenbos and Michael Yargosz

[21] Appl. No.: 866,779

[22] Filed: May 30, 1997

[51] Int. Cl.⁶ .................................................. A61B 17/00
[52] U.S. Cl. ........................................... 600/231; 600/235
[58] Field of Search ..................................... 600/201, 227, 600/228, 229, 231, 232, 233, 235, 230

[56] References Cited

U.S. PATENT DOCUMENTS

| | | |
|---|---|---|
| 605,715 | 6/1898 | Hohmann . |
| 1,375,445 | 4/1921 | Crossley . |
| 1,465,259 | 8/1923 | Friedman . |
| 1,517,915 | 12/1924 | Masland . |
| 3,749,088 | 7/1973 | Kohlmann . |
| 3,965,890 | 6/1976 | Gauthier . |
| 4,254,763 | 3/1981 | McCready et al. . |
| 4,421,108 | 12/1983 | Cabrera et al. . |
| 4,424,724 | 1/1984 | Bookwalter et al. ..................... 74/540 |
| 4,467,791 | 8/1984 | Cabrera et al. . |
| 4,617,916 | 10/1986 | LeVahn et al. . |
| 4,718,151 | 1/1988 | LeVahn et al. . |
| 4,813,401 | 3/1989 | Grieshaber . |
| 5,307,790 | 5/1994 | Byrne ..................................... 600/206 |
| 5,443,464 | 8/1995 | Russell et al. ............................ 606/54 |

OTHER PUBLICATIONS

Instruments designed by Orthopedic Surgeons—Innomed, Inc.—JBJS, Jun. 1995.
Instruments designed by Orthopedic Surgeons since 1987—Innomed, Inc.—c1996.

Primary Examiner—Jeffrey A. Smith
Attorney, Agent, or Firm—Margaret L. Geringer

[57] ABSTRACT

The invention is directed to an orthopaedic retractor frame assembly 10 for use during orthopaedic surgery at an incision site associated with a limb of a patient. The retractor frame assembly 10 includes a retractor frame 16 for placement adjacent the incision site. A limb attachment device 22 is connected to the retractor frame 16 and is configured for connection with a limb of the patient, whereby the retractor frame 16 is held at a desired orientation relative to the incision site. In addition, the retractor frame assembly 10 provides for retractor instruments 18 to be adjustably positioned relative to the retractor frame 16.

14 Claims, 3 Drawing Sheets

ORTHOPAEDIC RETRACTOR FRAME ASSEMBLY

BACKGROUND OF THE INVENTION

1. Field of the Invention

The present invention relates to an orthopaedic retractor frame assembly, and, more particularly, to an orthopaedic retractor frame assembly used to engage soft tissue at an incision site during orthopaedic surgery on a limb.

2. Description of the Related Art

A retractor frame assembly used during surgery typically includes a retractor frame which surrounds an incision site, such as an abdominal incision, and is connected at a plurality of locations to a plurality of corresponding retractor instruments, such as a rake, fakuda retractor, bone hooks, etc. The retractor frame is typically held in position relative to the incision site by rigidly connecting the retractor frame with a substantially immovable support structure, such as the table on which the patient is positioned. However, with such a retractor frame assembly, the table may need to be specially equipped for interconnection with the retractor frame assembly; the retractor frame assembly may not be easily positioned adjacent the incision site depending upon the particular location of the incision; the necessary support structure for the retractor frame assembly may be relatively bulky and cumbersome; and the patient may not be easily repositioned since the retractor frame assembly does not move with the patient.

It is known to provide a retractor frame which is only supported by opposing forces created by the use of the retraction instruments. To wit, retraction instruments may be attached to opposite sides of the retractor frame such that radially inward forces are exerted on the retractor frame at various locations about the periphery thereof. Such an apparatus may be adequate for certain surgical applications, but may be inadequate for other surgical applications depending upon the location of the surgical incision site and the ability to retract the incision about the periphery thereof.

It is also known to provide a head gear which is disposed over the crown of the head of a patient during surgery on an eye, and provides a frame to which instruments may be attached to maintain the eye lids in the open position and allow easy access to the eye ball.

In addition, with conventional retractor frame assemblies, the retractor instruments attached thereto typically cannot be easily positioned at different angular orientations relative to the incision site. It is known to provide a ratchet mechanism for interconnecting the retractor frame to a selected retractor instrument. The ratchet mechanism allows the retractor instrument to be moved in an axial direction away from the surgical incision site and prevents undesired movement of the retractor instrument in a direction toward the surgical incision site. However, such a ratchet mechanism does not allow the angular orientation between the retractor frame and the retractor instrument to be easily adjusted.

What is needed in the art is a retractor frame assembly which may be used during orthopaedic surgery and allows easier and more precise retraction of a surgical incision.

SUMMARY OF THE INVENTION

The present invention provides a retractor frame assembly which is attachable to a limb of the patient, and thereby does not require attachment to a table or other external supporting structure during use.

The invention comprises, in one form thereof, an orthopaedic retractor frame assembly for use during orthopaedic surgery at an incision site associated with a limb of a patient. The retractor frame assembly includes a retractor frame for placement adjacent the incision site. A limb attachment device is connected to the retractor frame and is configured for connection with a limb of the patient, whereby the retractor frame is held at a desired orientation relative to the incision site.

The invention comprises, in another form thereof, a ratchet clamp assembly for use with an orthopaedic retractor frame assembly including a retractor frame and a retractor instrument. The ratchet clamp assembly includes a first body with a frame receiving opening for receiving and attachment with the retractor frame. The frame receiving opening defines an axis about which the first body is rotatable when the retractor frame is disposed within the frame receiving opening. A second body includes a retractor receiving opening for receiving the retractor instrument therein. The second body is pivotally connected to the first body about an axis which is transverse to the axis of the frame receiving opening.

An advantage of the present invention is that the retractor frame is supported at a desired orientation relative to an incision site, without the necessity for additional supporting structure such as a table, etc.

Another advantage is that the retractor instrument may be positioned at a plurality of different angular orientations relative to the retractor frame.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
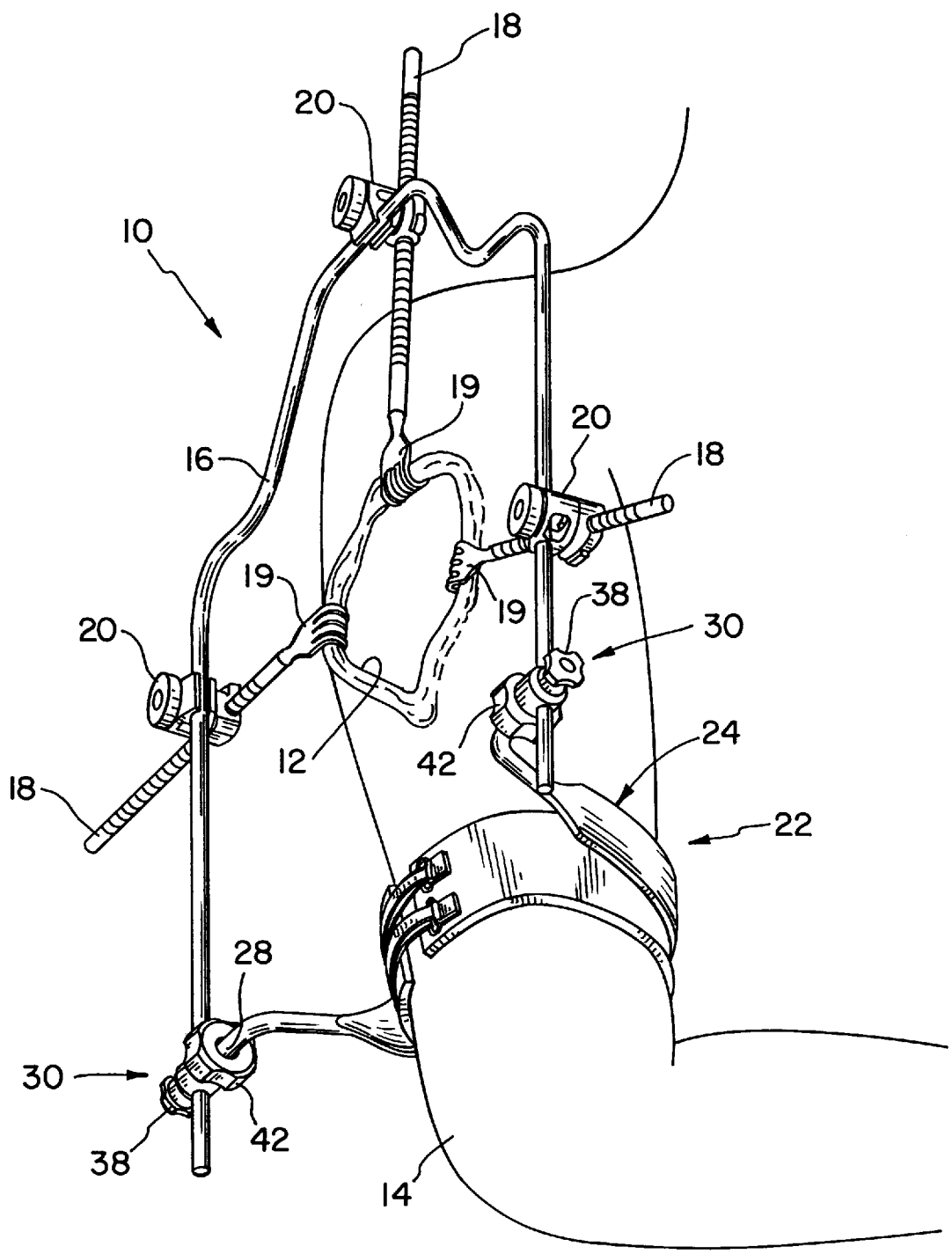
FIG. 1 is a perspective view of an embodiment of an orthopaedic retractor frame assembly of the present invention, when attached to a limb of a patient.

Referring now to the drawings and more particularly to FIG. 1, there is shown an embodiment of an orthopaedic retractor frame assembly 10 of the present invention for use during orthopaedic surgery at an incision site 12 associated with an arm or limb 14 of a patient. Retractor frame assembly 10 generally includes a retractor frame 16, retractor instruments 18, ratchet clamp assemblies 20, and limb attachment device 22.

Frame 16, in the embodiment shown, is in the form of a rod which has a circular cross-section and is formed to a particular shape. Retractor frame 16 may be generally U-shaped, as shown, or may include another desired shape such as a circular or rectangular shape. When used on an upper arm as shown in FIG. 1, frame 16 slopes away superiorly to avoid contact with the patients head.

According to one aspect of the invention, and referring now to FIGS. 1–4, conjunctively, limb attachment device 22 will now be described in greater detail. In the embodiment shown, limb attachment device 22 is in the form of a cuff assembly 22 which is connected to retractor frame 16, and which is configured for connection with limb 14 of the patient whereby retractor frame 16 is held at a desired orientation relative to incision site 12. More particularly, cuff assembly 22 includes a cuff frame 24 having a generally U-shaped portion 26 and opposing ends 28. U-shaped portion 26 partially surrounds limb 14 of the patient, as shown in FIG. 1.

Cuff frame 24 of cuff assembly 22 is selectively connected to cuff frame 16 at two selected locations using locking devices 30 which are attached to respective opposing ends 28 of cuff frame 24. Locking devices 30, shown in detail in FIGS. 2 and 3, include a body 32 having a frame receiving opening 34 and a frustroconical opening 36. Retractor frame 16 is slidably received within frame receiving opening 34. A thumb nut 38 is threaded into the end of body 32 (not shown), and applies an axial load to retractor frame 16 to lock body 32 at a desired position relative to retractor frame 16.

Frustroconical opening 36 receives opposing end 28 of cuff frame 24 therein. In particular, end 28 of cuff frame 24 includes a frustroconical end 40 having a shape which is complementary to that of frustroconical opening 36 in body 32. A lock nut 42 is threadingly engaged with body 32 and biases frustroconical end 40 in an axial direction into frustroconical opening 36. The angular orientation between cuff frame 24 and body 32 can thus be varied and locked into position by tightening lock nut 42.

Figure 2:
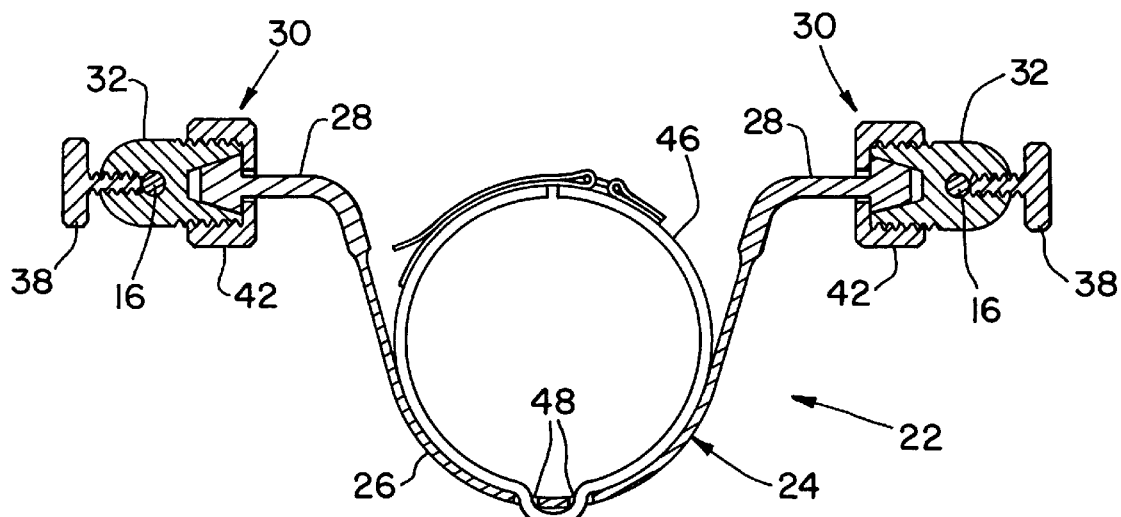
FIG. 2 is a side sectional view of the orthopaedic retractor frame assembly shown in FIG. 1, taken through the cuff assembly.
Figure 3:
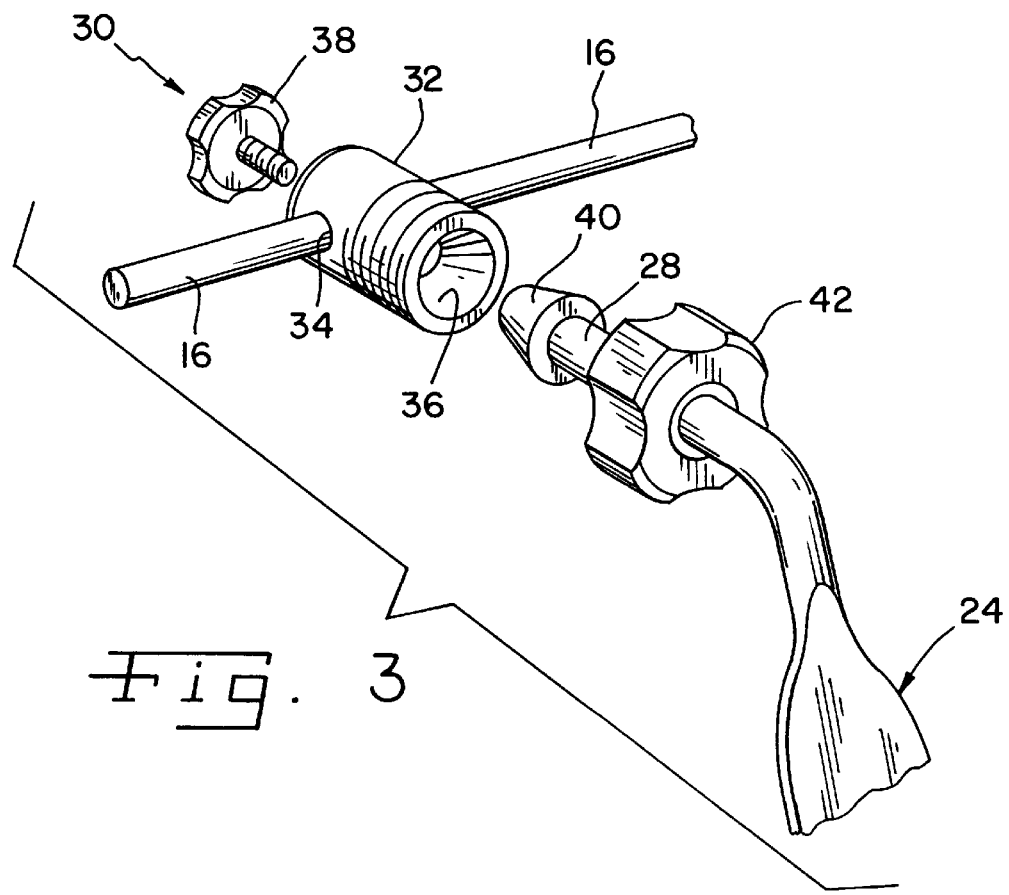
FIG. 3 is an exploded view of a locking device shown in FIGS. 1 and 2, which is used for interconnecting the cuff frame with the retractor frame.
Figure 4:
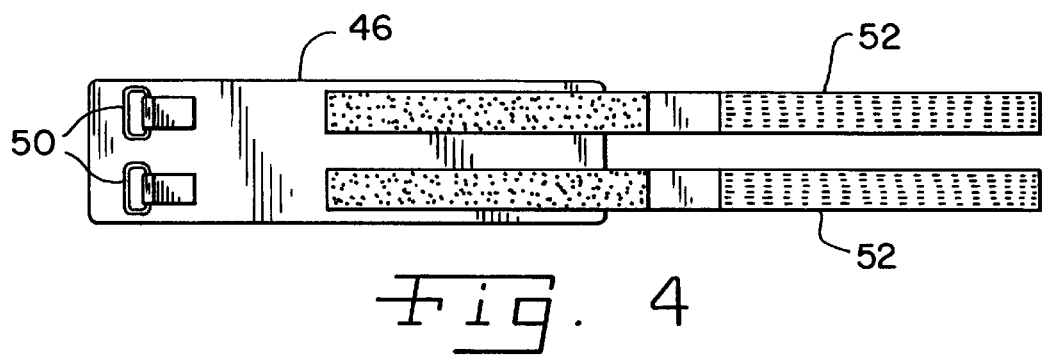
FIG. 4 is a plan view of the cloth cuff shown in FIGS. 1 and 2.

Cuff assembly 22 also includes a cloth cuff 46 which is connected to cuff frame 24 by passing through openings 48 (FIG. 2) formed in cuff frame 24. Cuff 46 is configured for placement around and attachment to limb 14 of the patient, as shown in FIG. 1. More particularly, referring to FIGS. 2 and 4, cuff 46 includes eyes 50 attached to one end thereof and hook and loop fasteners 52 attached to an opposing end thereof. Each hook and loop fastener 52 is passed through a respective eye 50 and folded back on itself as shown in FIG. 2 to connect the opposing ends of cuff 46 to each other. In the embodiment shown, hook and loop fasteners 52 are in the form of Velcro ® fasteners. Of course, cuff 46 may also be formed such that the hook fasteners are on one end thereof and the loop fasteners are on the opposing end thereof.

Figure 5:
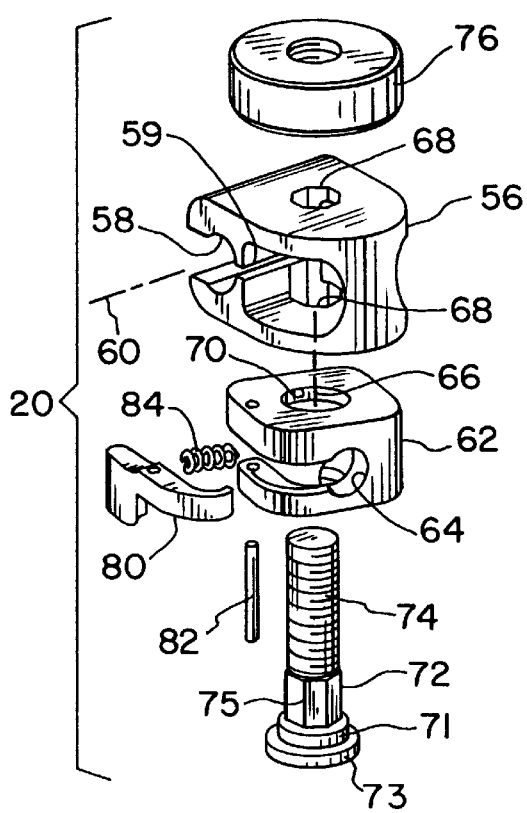
FIG. 5 is an exploded view of a ratchet clamp assembly shown in FIG. 1, which is used for interconnecting a retractor instrument to the retractor frame.
Figure 6:
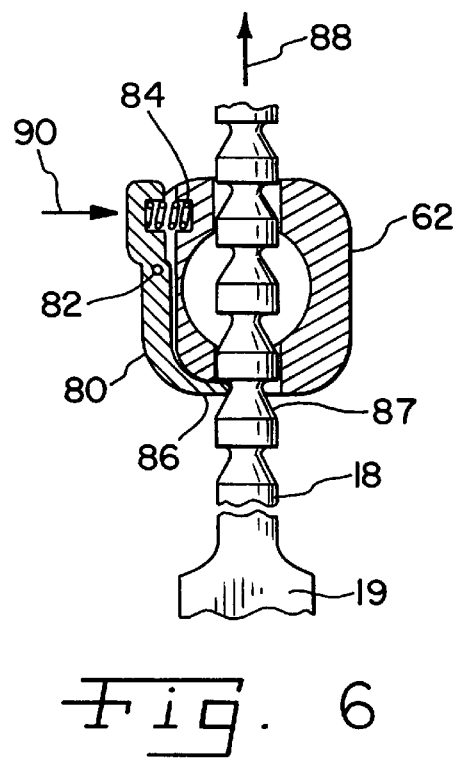
FIG. 6 is a top, sectional view of the ratchet clamp assembly shown in FIG. 5, when assembled.

Referring now to FIGS. 5 and 6, ratchet clamp assemblies 20 shown in FIG. 1 will be described in greater detail. Each ratchet clamp assembly 20 is used as a frame interconnection device for interconnecting a retractor instrument 18 with retractor frame 16. Retractor instrument 18 may be in the form of a rake (as shown), a bone hook, a Darrach retractor, a Fakuda retractor, a Richardson retractor, etc.

Each ratchet clamp assembly 20 allows the positioning of a respective retractor instrument 18 about two separate axes relative to retractor frame 16. More particularly, ratchet clamp assembly 20 includes a first body or clip-on body 56 having a frame receiving opening 58 for receiving and attachment with retractor frame 16. Frame receiving opening 58 defines an axis 60 about which first body 56 is rotatable when retractor frame 16 is disposed within frame receiving opening 58. That is, first body 56 is rotatable about retractor frame 16 when engaged therewith.

A second body or ratchet body 62 includes a retractor receiving opening 64 for receiving a retractor instrument 18 therein. Second body 62 is pivotally connected to first body 56 about an axis 66 which is substantially perpendicular to axis 60 associated with frame receiving opening 58. More particularly, each of first body 56 and second body 62 includes a bolt receiving opening 68, 70, respectively, therein. A bolt 72 extends through bolt receiving openings 68, 70 and is positioned substantially coaxially with axis 66 defined by bolt receiving opening 70. Bolt 72 includes a threaded end 74 which extends through bolt receiving opening 68 formed in first body 56, and is threadingly engaged with a thumb nut 76. Thumb nut 76 may be tightened against first body 56 such that frame receiving opening 58 is tightened about frame 16 to restrict or inhibit rotation of first body 56 about axis 66 by compressing the slit 59 in opening 58. The second body 62 continues to be rotatable relative to first body 56. Second body 62 rotates about the cylindrical portion 71 and enlarged cylindrical head 73 of bolt 72. The enlarged head 73 forms a shoulder to retain bolt 72 in bolt receiving opening 70. The hexagonal portion 75 of bolt 72 mates with hexagonal opening 68 in first body 56, to prevent relative movement between body 56 and bolt 72.

Referring now to FIG. 6, details of a ratchet 80 which engages a retractor instrument 18 are shown. Ratchet 80 is pivotally connected to second body 62 using a pivot pin 82. A compression spring 84 biases ratchet 80 to the position shown in FIG. 6, whereby an end 86 of ratchet 80 is in engagement with one of a plurality of grooves 87 formed in retractor instrument 18. As will be appreciated, retractor instrument 18 may be moved in an axial direction 88; however, ratchet 80 prevents axial movement of retractor instrument 18 in a direction opposite axial direction 88 indicated in FIG. 6. Upon completion of a retraction procedure, retractor instrument 18 may be moved in a direction opposite to axial direction 88 by depressing ratchet 80 as shown by directional arrow 90 in FIG. 6, thus releasing end 86 from engagement with grooves 87 of retractor instrument 18. It will be apparent from the foregoing description that each ratchet clamp assembly 20 is thus adjustable about two separate axes relative to retractor frame 16, and thereby allows proper positioning of an associated retractor instrument 18 relative to incision 12. In addition, if desired, the grooves 87 on retractor instrument 18 may be circumferential grooves, as shown, which enable the retractor instrument 18 to rotate about its elongated axis. This allows the distal working end 19 to be adjustably rotated, as desired.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic retractor frame assembly for use during orthopaedic surgery at an incision site associated with a limb of a patient, said retractor frame assembly comprising:
   a retractor frame for placement adjacent the incision site; and
   a limb attachment device connected to said retractor frame, said limb attachment device being configured for connection with a limb of the patient whereby said retractor frame is held at a desired orientation relative to the incision site, wherein said limb attachment device comprises a cuff assembly including a cuff frame and a cuff, said cuff frame connected to said retractor frame, said cuff connected to said cuff frame and being configured for placement around and attachment to the limb of the patient.

2. The orthopaedic retractor frame assembly of claim 1, wherein said cuff frame is connected to said retractor frame at two locations.

3. The orthopaedic retractor frame assembly of claim 2, further comprising two locking devices interconnecting said cuff frame with said retractor frame at said two locations.

4. The orthopaedic retractor frame assembly of claim 3, wherein said cuff frame includes two opposing ends, and wherein each said locking device comprises a body having a frame receiving opening and a frustroconical opening, said retractor frame disposed within each said frame receiving opening and each said cuff frame end disposed within a respective said frustroconical opening.

5. The orthopaedic retractor frame assembly of claim 4, wherein each said cuff frame end comprises a frustroconical end, and wherein each said locking device further comprises a lock nut for biasing said frustroconical end into said respective frustroconical opening.

6. The orthopaedic retractor frame assembly of claim 1, wherein said cuff frame is connectable at selected locations to said retractor frame.

7. The orthopaedic retractor frame assembly of claim 1, wherein said cuff frame comprises a generally U-shaped portion for partially surrounding the limb of the patient, and wherein said cuff comprises a cloth cuff attached to said U-shaped portion.

8. The orthopaedic retractor frame assembly of claim 7, wherein said cloth cuff includes hook and loop fasteners for connecting opposing ends of said cloth cuff to each other.

9. The orthopaedic retractor frame assembly of claim 1, wherein said retractor frame is configured to at least partially surround the incision site.

10. The orthopaedic retractor frame assembly of claim 1, further comprising a plurality of retractor instruments and a plurality of frame interconnection devices for respectively interconnecting said retraction instruments with said retractor frame.

11. The orthopaedic retractor frame assembly of claim 10, wherein each said frame interconnection device is configured to allow positioning of a respective said retractor instrument about two separates axes relative to said retractor frame.

12. An orthopaedic retractor frame assembly for use during orthopaedic surgery at an incision site associated with a limb of a patient, said retractor frame assembly comprising:
   a retractor frame for placement adjacent the incision site; and
   means for attaching said retractor frame with a limb of the patient whereby said retractor frame is held at a desired orientation relative to the incision site, wherein said limb attaching means comprises a cuff assembly including a cuff frame and a cuff, said cuff frame connected to said retractor frame, said cuff connected to said cuff frame and being configured for placement around and attachment to the limb of the patient.

13. The orthopaedic retractor frame assembly of claim 12, wherein said cuff frame comprises a generally U-shaped portion for partially surrounding the limb of the patient, and wherein said cuff comprises a cloth cuff attached to said U-shaped portion.

14. The orthopaedic retractor frame assembly of claim 13, wherein said cloth cuff includes hook and loop fasteners for connecting opposing ends of said cloth cuff to each other.

* * * * *